United States Patent [19]

Sisley et al.

[11] 4,405,313
[45] Sep. 20, 1983

[54] FIGURE-EIGHT, DUAL-LUMEN CATHETER AND METHOD OF USING

[76] Inventors: James R. Sisley, 3450 Evergreen Point Rd., Bellevue, Wash. 98004; Robert O. Hickman, 11100 Kulshan Dr., Edmonds, Wash. 98020

[21] Appl. No.: 343,736

[22] Filed: Jan. 29, 1982

[51] Int. Cl.³ .............................................. A61M 5/00
[52] U.S. Cl. ...................................... 604/43; 604/53; 604/264; 604/280
[58] Field of Search ................................... 604/27–29, 604/53, 93, 264, 39, 43–45, 280–284, 173

[56] References Cited

U.S. PATENT DOCUMENTS

| | | | |
|---|---|---|---|
| 2,286,462 | 6/1942 | Chaffin | 604/43 |
| 3,114,373 | 12/1963 | Andersen | 604/45 |
| 3,495,595 | 2/1970 | Soper | 604/28 |
| 3,633,585 | 1/1972 | McDonald, Jr. | 604/29 |
| 4,168,703 | 9/1979 | Kenigsberg | 604/45 X |
| 4,211,233 | 7/1980 | Lin | 604/43 |
| 4,300,550 | 11/1981 | Gandi et al. | 604/45 X |
| 4,364,394 | 12/1982 | Wilkinson | 604/39 X |

Primary Examiner—Richard J. Apley
Assistant Examiner—Michelle N. Lester
Attorney, Agent, or Firm—Seed, Berry, Vernon & Baynham

[57] ABSTRACT

An improved figure-8, dual-lumen catheter preferably includes substantially convex, smooth, smoothly curving fill-in portions at the point of entry to the vessel and the point of entry to the skin to virtually eliminate blood leakage from the vessel and to reduce bacterial passage into the patient along the catheter. Preferably, a felt cuff is positioned substantially midway between the point of entry to the skin and point of entry to the vessel to promote tissue in-growth which will fix the catheter within the patient. A method for surgically implanting the preferred catheter of this invention is also disclosed. In some applications, a single fill-in portion may be used if it is sufficiently long that it provides a convex contact between the vessel and the catheter and between the skin and the catheter.

40 Claims, 4 Drawing Figures

FIGURE-EIGHT, DUAL-LUMEN CATHETER AND METHOD OF USING

TECHNICAL FIELD

The present invention relates to an improved figure-8, dual-lumen catheter and a method of surgically implanting the catheter which reduces the complications of infection and fluid leakage.

BACKGROUND ART

Often, medications are given by mouth or by intramuscular, intravascular, or intravenous injection. With larger doses or with a continuing dose, intravascular or intravenous (IV) application may be used. IV's are problematic because they often lead to hematomas on or other irritation to the patient and cause vessels to collapse. When used over an extended period of time, they can be traumatic and unreliable for the patient.

Single lumen catheters have been used, with or without surgical implantation, to convey fluids.

During the last decade, it became popular to use surgically implanted catheters to allow more reliable and dependable monitoring of conditions and application of medications. Single-lumen and dual-lumen tubes have been used. Usually the dual-lumen tubes have a cylindrical outside periphery and an internal wall to separate the lumen into two portions. These catheters are more rigid than desirable and have pressure limitations which limit the uses of the catheter. Control of the separate channel sizes can be difficult. Figure-8, dual-lumen catheters have side-by-side tubes so that each catheter resembles a double-barrel shotgun of the over-and-under variety. The tubes are connected so that grooves appear on each side of the catheter. When implanted into vessels, the first figure-8, dual-lumen catheter leaked vessel fluids and allowed bacteria to enter the patient along the grooves of the catheter tubes. The blood leakage problem was stopped by filling in a portion to the figure-8, dual-lumen catheter at the point where the catheter passed through the vessel. When used, the patients were still subject to increased incidence of infection.

DISCLOSURE OF INVENTION

The present invention relates to a surgically implanted, figure-8, dual-lumen catheter which is improved by placing a second fill-in portion at the point of contact beteween the skin and the catheter. This second fill-in portion has been found to substantially reduce the passage of bacteria along the catheter into the patient. Infections are dramatically reduced. The fill-in portions are substantially convex, substantially smoothly curving portions applied in segments on opposite sides of the catheter to fill the grooves. These fill-in portions allow more substantial contact between the patient's tissues and the catheter to provide natural sealing.

A novel method of implanting the figure-8, dual-lumen catheter of this invention is also disclosed. Surgically implanted catheters are intended to remain within the patient for an extended period of time and are designed to reduce trauma in the critically ill patient who needs medication, blood products, and other treatments periodically. The trauma caused by surgically implanting the catheter is outweighed by the advantages obtained by having direct access to major vessels for treatment. That is, over time, the surgically implanted catheter reduces trauma. Implanting the catheter requires creating of a subcutaneous tunnel from a point of entry at the skin to a point of entry to the vessel (e.g., a vein or artery). Generally, the subcutaneous tunnel is between 4 to 6 inches in length (about 10–15 cm). The plastic, figure-8, dual-lumen catheter is inserted through the subcutaneous tunnel into the vessel. At the point of contact between the vessel and catheter, a substantially convex, smoothly curving fill-in portion contacts the vessel. Similarly, at the point of contact with contact with the skin, a second substantially convex, smoothly curving portion is used. The first fill-in portion, usually with a ligature (suture) at the vessel, relieves the problem of fluid leakage at the vessel. The second fill-in portion relieves the problem of bacterial passage along the catheter. Ordinarily, intermediate between the two fill-in portions, a felt cuff helps to reduce the passage of bacteria along the catheter and promotes tissue in-growth to fix the position of the catheter within the patient.

Surgically implanted catheters allow the critically ill patient to move more freely than regular intravenous injections allow, and allow direct access to critical areas for providing fast and dependable treatment. Dual-lumen catheters are multipurpose and provide access for the simultaneous application of medications and blood products. In a particularly desirable application of surgically implanting the figure-8, dual-lumen catheters, the tip of the catheter is positioned within the superior vena cava or the right atrium so that medication and blood products may be delivered directly to a high flow area and monitoring can be done directly.

In summary, the catheter of this invention preferably has a pair of side-by-side plastic tubes forming a figure-8, dual-lumen catheter body and fill-in portions forming smooth convex surfaces at the points of contact between entry to the skin and entry to the vessel. Preferably, the convex surfaces are generally oval in cross-section and the tubes have different diameters. The larger tube should be just large enough to allow the drawing of blood from the patient. Blood drawing is usually achievable with a lumen (inside diameter of the tube) of about 1.6 mm diameter. A felt cuff is ordinarily positioned substantially midway between the point of contact of the fill-in portion with the vessel and the point of contact with the second fill-in portion with the skin. The figure-8, dual-lumen catheter body is generally formed by extruding medical-grade silicon rubber into two tubes. The fill-in portions are compatible plastic segments and are usually positioned on opposite sides of the catheter body. To avoid in-growth of tissue into the matrix of the fill-in portions, the fill-in portions are generally polished, to be as smooth as the tubes.

BEST MODE FOR CARRYING OUT THE INVENTION

Figure 1:
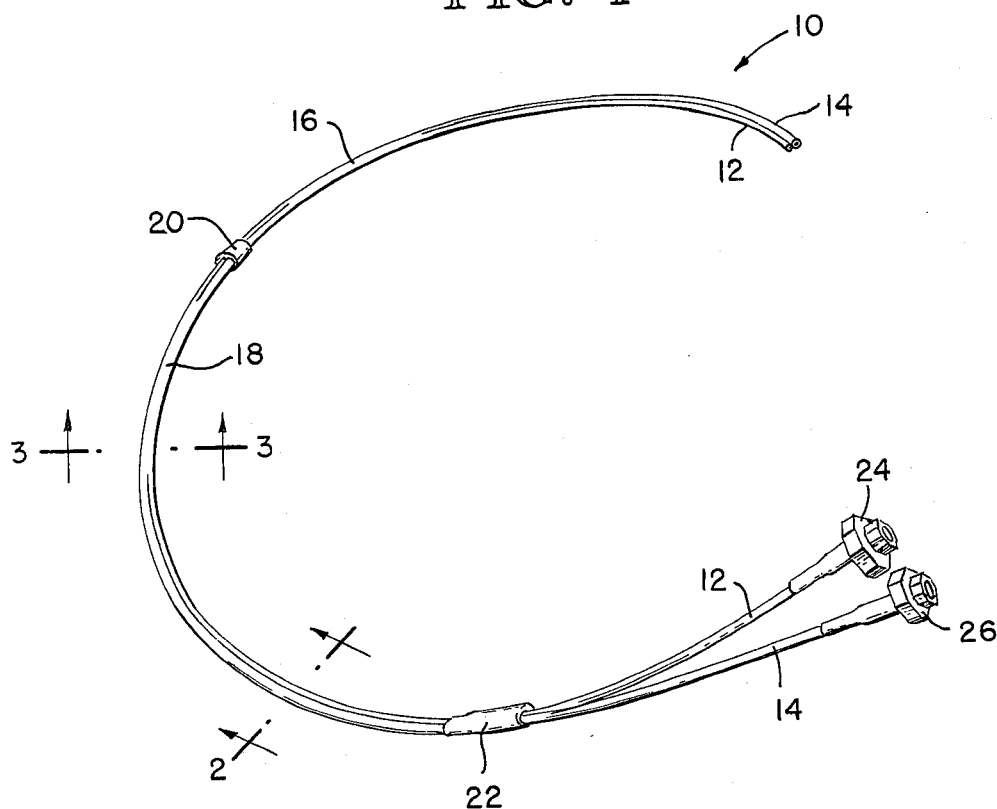
FIG. 1 is a perspective view of a preferred figure-8, dual-lumen catheter of this invention.

Basically, the figure-8, dual-lumen catheter of this invention improves performance by placing substantially convex, smooth, smoothly curving fill-in portions at the points of contact between the skin and vessel. The fill-in portion at the vessel virtually eliminates fluid leakage around the catheter when the vessel is secured with a ligature. Typically, ligatures are used, although they may not be essential to stop leakage from the vessel. The fill-in portion at the point of contact with the skin reduces the passage of bacteria along the catheter body into the patient and thereby reduces the chance of infection for the patient.

Surgically implanted catheters were developed primarily to provide multipurpose access to the critically ill patient so that all medications and blood products could be applied simultaneously.

The preferred catheter includes a body portion having two, side-by-side tubes attached together. The tubes form the basic figure-8, dual-lumen body through which medications and blood products may be provided to the patient or through which blood may be drawn from the patient. The tubes are preferably durable, flexible, nontoxic, and biologically neutral. They should be able to withstand autoclave sterilization and be essentially insensitive to medications (that is, the tubes are essentially nonadsorbent and essentially nonabsorbent). The tubes may be either radiopaque or invisible to X-rays, depending on the desired use. Generally, the tubes are elastomeric polymers, such as medical-grade silicon rubber. While silicon rubber is preferred, polyvinyl chloride, polyethylene, natural or synthetic rubber, or other suitable polymers may be used. Preferably, the tubes of the catheter have different lumen diameters. The larger tube of the pair is generally just large enough to allow drawing blood from the patient. In most applications, then, this tube has an inside diameter no greater than about 1.6 mm. The second tube is generally smaller, usually in the range of about 1.0 mm I.D.

Dual-lumen catheters of the figure-8 conformation allow multipurpose venous access for the critically ill patient so that all medications and blood products may be applied simultaneously. Often, a patient requires both constant medication or blood transfusion and sporadic application of other medications. The dual-lumen catheter allows the continuous infusion of one fluid and the sporadic infusion of others. Also, the dual-lumen catheter allows continuous infusion of a fluid while blood is being drawn from the patient. Surgically implanted catheters allow greater freedom of movement for the patient who no longer needs to worry as greatly about dislodging the IV needle and allow more rapid access to critical areas for critical treatments.

Early experiments with figure-8, dual-lumen catheters were unsuccessful because of a high incidence of infection and an inordinate fluid loss. To overcome these problems, substantially convex, smoothly curving fill-in portions were placed around the figure-8, dual-lumen catheter body at the points of contact between the vessel with the catheter and the skin with the catheter. At the vessel, combined with a ligature, the fill-in portion substantially eliminates fluid leakage. At the skin, the fill-in portion reduces passage of bacteria along the groove otherwise formed in the catheter.

Ordinarily, the catheter has a Dacron felt cuff positioned between the fill-in portions. For a right atrial catheter, the cuff is approximately 5 cm above the end of the fill-in portion which will enter the vein. To ensure that there is contact between the vessel and the convex outer surface, the fill-in portion is preferably approximately 4 cm in length to provide the doctor with approximately 1-inch leeway in implanting the catheter. The length of the fill-in portion is given by way of example rather than by way of limitation. If the ligature around the vein should fall outside the fill-in portion of the dual-lumen catheter, blood will seep retrograde up the grooves and will cause excessive blood loss.

Within the vein, it is preferable that the catheter be substantially entirely of the figure-8, dual-lumen conformation. That is, as little as possible of the fill-in portion should enter the vein. The figure-8, dual-lumen catheter is more flexible than the earlier cylindrical design, which included a rigid wall within the inside area of the tube, and is less intrusive within the vessel because the grooves create spaces between the catheter and the wall of the vessel which allow easier flow of fluid within the vessel. That is, the figure-8, dual-lumen conformation occupies the minimum volume necessary within the vessel to achieve the function of multipurpose access.

Speed approximately equally distant above the cuff as that fill-in portion below the cuff, a second fill-in portion provides a bacterial seal between the point of entry to the skin and the catheter. This second fill-in portion can extend over substantially the entire remaining length of the catheter, although as short a fill-in as possible is preferred to provide the maximum flexibility of the catheter and to reduce manufacturing costs. As with the first fill-in portion, this fill-in portion provides a substantially convex, smooth, substantially smoothly curving outer surface upon which the skin tissue rests to provide a natural seal which reduces bacterial transport along the catheter.

In some circumstances, it is possible that only one fill-in portion be used. In this case, the fill-in portion should be sufficiently long to allow contact at the vessel and at the skin. The cuff will be positioned substantially midway between the point of entry to the vessel and the point of entry to the skin to provide maximum security for implantation of the catheter.

Figure 3:
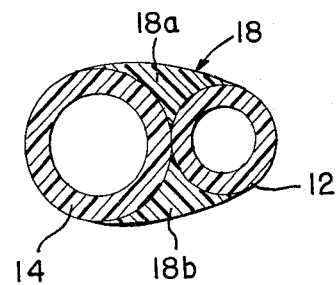
FIG. 3 is a typical cross-section of a fill-in portion of the catheter taken along line 3—3 of FIG. 1.

Each fill-in portion is preferably bonded by adhesion to the extruded silicon rubber tubes which form the figure-8, dual-lumen catheter body. Preferably, silicon rubber is applied in two segments to achieve a generally oval shape, as shown in FIG. 3.

Figure 2:
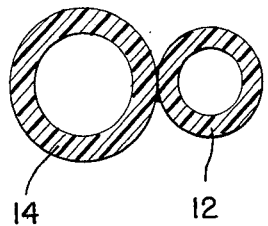
FIG. 2 is a typical cross-section of the figure-8, dual-lumen catheter taken along line 2—2 of FIG. 1.

Referring now to the drawings, FIG. 1 shows a figure-8, dual-lumen catheter 10 having two, connected side-by-side tubes 12 and 14. The figure-8, dual-lumen catheter 10 is preferably formed by extruding medical-grade silicon rubber into the figure-8 conformation, which is shown the best in FIG. 2. Preferably, the tubes 12 and 14 have different lumen diameters (as best shown in FIG. 2). The larger tube 14 preferably has an inside diameter just large enough for the drawing of blood from the patient. Usually this tube will have an inside diameter of about 1.6 mm. The smaller tube can be of any dimension, but it is generally about 1.0 mm inside diameter. These ranges should not be limiting. Catheters for use in premature babies are envisioned, and these catheters will have tubes as small as 0.010 inch inside diameter. Also, catheters for access to the aorta are also contemplated and these catheters would have two tubes of equal diameter, approximately ½ inch inside diameter per tube.

Two fill-in portions 16 and 18 are found along the length of the preferred catheter 10. Both fill-in portions 16 and 18 are analogous and are shown in typical cross-section in FIG. 3. Basically, each fill-in portion 18 includes two segments 18a and 18b positioned on opposite sides of the figure-8 to substantially fill the groove and to form a generally oval outer locus for the catheter. To provide reduction of fluid leakage and reduction of bacterial passage, the outer surface of the catheter should be a substantially convex, substantially smoothly curving section, such as the oval shown in FIG. 3. Other smoothly curving, convex shapes are also contemplated as being useful in this invention, such as circles, ellipses, or other generally smoothly curving loci. Discontinuities in slope, as shown by the groove of the figure-8, dual-lumen body or as provided by a corner in such shapes as a rectangle or triangle, should be avoided because it is at this discontinuity of slope that fluid leakage or bacterial passage occurs. The tissue is not able to seal at the abrupt change which a corner provides.

Intermediate between the fill-in portions 16 and 18 and substantially midway between the point of entry to the skin and the point of entry to the vessel, a felt cuff 20 is positioned to provide a further security against the passage of bacteria along the surface of the dual-lumen catheter and to promote tissue in-growth, which will fix the catheter within the patient.

Toward the exposed end of the catheter (that end which does not enter the patient) is found is a splitter 22 which wraps the junction of the tubes 12 and 14, which separates the tubes 12 and 14, and which eliminates further splitting of the tubes 12 and 14.

With the tubes split, luer lock connectors 24 and 26 are attached to the tubes 12 and 14 to allow connection of the catheter to desired fluid reservoirs for infusion of medication or blood products, or for withdrawal of blood or other fluids from the patient.

Figure 4:
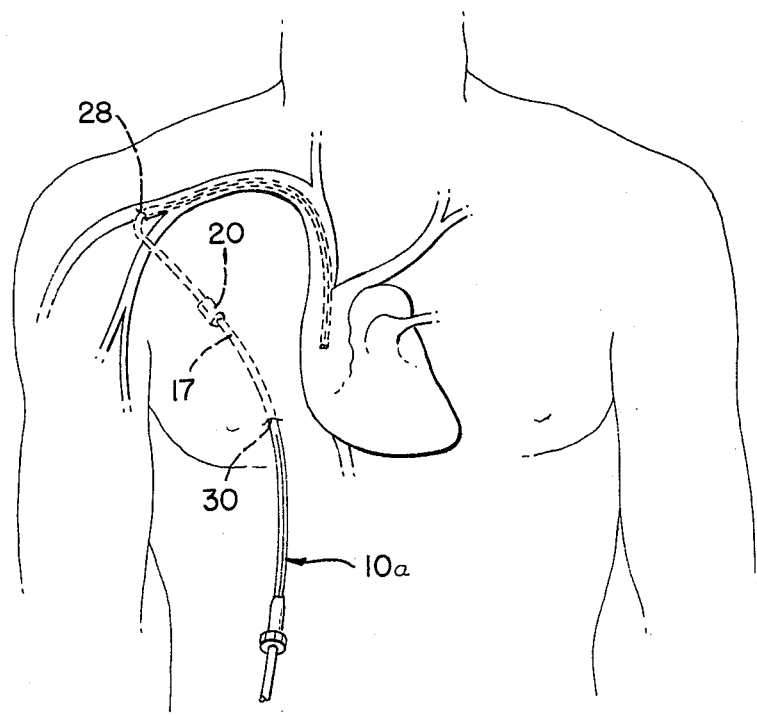
FIG. 4 is a schematic showing implantation of a catheter of this invention into the right atrium (or the superior vena cava).

FIG. 4 schematically illustrates the surgical implantation of an alternate figure-8, dual-lumen catheter 10a into the right atrium of a patient. A single fill-in portion 17 with an intermediate cuff 20 provides a substantially convex surface at the point of entry to the vein 28 (e.g., the cephalic vein) and the point of entry to the skin 30, as already described. Within the vein, the catheter is substantially entirely of the figure-8, dual-lumen conformation.

Before implantation, the catheter should be sterilized by steam autoclaving. Ethylene oxide sterilization is not recommended because of the necessity to avoid any possible effects of residual ethylene oxide within the catheter.

The catheter should be cut to length to suit the application. Where the catheter is used for blood withdrawal or infusion, the catheter length should be as short as practical to minimize flow resistance within the blood vessel. For application of medication, the tip of the catheter which will be inserted into the vessel preferably is cut on a bias, with the smaller diameter tube having a shortened end approximately 1 to 10 cm shorter than the larger lumen tube. Typically, the shorter tube will be between about 1 to 2 cm shorter. It has been found that the tip of this configuration seems to be the most practical, although there is little data to support this preference.

For insertion into the right atrium or the superior vena cava (SVC), the catheter should be measured so that the tip of the catheter will fall deep within the SVC into the entrance of the right atrium. The size of the dual-lumen catheter requires use of a fairly large vein for access to the right atrium. It is has been found that the external jugular veins on the right or left, or the cephalic veins on the right or left (for adults or larger teenagers), permit entry of the catheter into the atrium. Preferably, a subcutaneous tunnel of approximately 4 to 6 inches in length is prepared. The felt cuff 20 should be positioned along the catheter so that it will lie approximately midway between the point of exit from the skin and the point of entry to the vein. While use of the right external jugular is preferred for access to the right atrium, the cephalics, femoral, the internal jugulars, and other vessels are also possible candidates for entry.

While described with reference to surgically implanting the catheter for access to the right atrium, the figure-8, dual-lumen catheters of this invention are useful for many other purposes. In general terms, the catheter may be used to provide access to any body cavity, vessel, or passage, and may be sized to perform nearly any desired function. For example, the catheter may access blood vessels, the alimentary canal, the urethra, or the uterus. Unless the context necessarily restricts the meaning of "vessel," "vessel" should mean any body cavity or passage and should not be limited to arterial, venal, lymphatic, renal, or other circulatory vessels. The catheters are useful for human and animal treatment.

Although it is preferred to use silicon rubber fill-in portions for silicon rubber tubes, the fill-ins need only be compatible with the tubes. The primary restriction upon the fill-in portions, other than those already imposed upon the tubes, is that the fill-in portions should be bondable to the figure-8, dual-lumen body below the melt temperature of the body. If desired, the fill-in portions may be directly formed into the tubes during manufacture of the body.

I claim:

1. A dual-lumen catheter suitable for surgical implantation in a patient through a subcutaneous tunnel having a point of entry to the skin and a point of entry to the desired vessel, comprising:
   (a) two tubes attached side-by-side to form a figure-8, dual-lumen body;
   (b) a first fill-in portion on the body, having a substantially convex, smoothly curving outer locus and bridging the junction of said two tubes, positionable at the point of entry to the skin to reduce the passage of bacteria along the body;
   (c) a second fill-in portion on the body, having a substantially convex, smoothly curving outer locus and bridging the junction of said two tubes, positionable at the point of entry to the vessel to reduce blood leakage when the vessel is secured with a ligature; and
   (d) a cuff positionable between the point of entry to the skin and the point of entry to the vein to promote tissue in-growth which will fix the catheter within the patient after implantation.

2. The catheter of claim 1 wherein the first and second fill-in portions are connected with an intermediate fill-in portion so that the catheter appears to have only one fill-in portion which is sufficiently long to allow contact of the fill-in portion at both the point of entry to the skin and the point of entry to the vessel.

3. The catheter of claim 1 or claim 2 wherein the second fill-in portion ends substantially immediately after entry of the body into the vessel so that the portion of the catheter within the vessel is substantially entirely a figure-8, dual-lumen body.

4. The catheter of claim 1 or claim 2 wherein the cuff is positioned so that the cuff will be substantially midway between the point of entry to the skin and the point of entry to the vessel when the catheter is implanted.

5. The catheter of claim 1 or claim 2 wherein the cuff is a felt cuff.

6. The catheter of claim 1 wherein the tubes have different diameters so that there is a larger and a smaller tube.

7. The catheter of claim 6 wherein the larger tube has a lumen (inside diameter) large enough to allow drawing blood from the patient.

8. The catheter of claim 6 wherein the larger tube has a lumen just large enough to allow drawing blood from the patient.

9. The catheter of claim 6 wherein the larger tube has a lumen of at least about 0.063 inch (about 0.16 cm).

10. The catheter of claim 1 wherein at least one of the tubes has a lumen large enough to allow drawing blood from the patient.

11. The catheter of claim 6 wherein each fill-in portion makes the catheter generally oval in cross-section.

12. The catheter of claim 1 or claim 11 wherein the fill-in portions are smoothed to substantially eliminate tissue growth into the matrix of the fill-in portions.

13. The catheter of claim 1 wherein each fill-in portion includes bonded plastic segments attached to the body on opposite sides of the body.

14. A dual-lumen catheter suitable for surgical implantation in a patient through a subcutaneous tunnel having a point of entry to the skin and a point of entry to the vessel, comprising:
(a) two plastic tubes attached side-by-side to form a figure-8, dual-lumen body, wherein at least one tube has a lumen large enough to allow drawing blood from the patient;
(b) a first plastic fill-in portion bonded to the body, having a substantially convex, smoothly curving outer locus and bridging the junction of said two tubes, positionable at the point of entry to the skin to reduce the passage of bacteria along the body;
(c) a second plastic fill-in portion bonded to the body, having a substantially convex, smoothly curving outer locus and bridging the junction of said two tubes, positionable at the point of entry to the vessel to reduce blood leakage when the vessel is secured with a ligature; and
(d) a cuff positionable between the first and second fill-in portions between the point of entry to the skin and the point of entry to the vessel, when implanted, to promote tissue in-growth which will fix the catheter within the patient.

15. The catheter of claim 14 wherein the first and second fill-in portions are connected with an intermediate fill-in portion so that the catheter appears to have only one fill-in portion which is sufficiently long to allow contact of the fill-in portion at both the point of entry to the skin and the point of entry to the vessel.

16. The catheter of claim 14 of claim 15 wherein the second fill-in portion ends substantially immediately after entry of the body into the vessel so that the portion of the catheter within the vessel is substantially entirely a figure-8, dual-lumen body.

17. The catheter of claim 14 wherein the tubes have different diameters so that there is a larger and a smaller tube.

18. The catheter of claim 14 wherein each fill-in portion includes bonded plastic segments attached to the body on opposite sides of the body.

19. A dual-lumen catheter suitable for surgical implanation in a patient through a subcutaneous tunnel having a point of entry to the skin and a point of entry to the vessel, comprising:
(a) two plastic tubes attached side-by-side to form a figure-8, dual-lumen body, wherein at least one tube has a lumen large enough to allow drawing blood from the patient;
(b) a first plastic fill-in portion bonded to the body in segments attached to the body on opposite sides of the figure-8 to provide a substantially convex, smoothly curving outer locus and bridging the junction of said two tubes, positionable at the point of entry to the skin to reduce the passage of bacteria along the body, and having a smoothed surface to substantially eliminate tissue growth into the matrix of the fill-in portion;
(c) a second plastic fill-in portion bonded to the body, spaced away from the first fill-in portion by an intermediate section of the body, having segments attached to the body on opposite sides of the figure-8 to provide a substantially convex, smoothly curving outer locus and bridging the junction of said two tubes, positionable at the point of entry to the vessel to reduce blood leakage when the vessel is secured with a ligature, and having a smoothed surface to substantially eliminate tissue growth into the matrix of the fill-in portion; and
(d) a cuff positionable on the intermediate section between the first and second fill-in portions to be between the point of entry to the skin and the point of entry to the vessel to promote tissue in-growth which will fix the catheter within the patient after implantation and which will reduce the passage of bacteria along the intermediate section.

20. The catheter of claim 19 wherein the cuff is positioned substantially midway between the point of entry to the skin and the point of entry to the vessel upon implantation.

21. The catheter of claim 19 wherein the cuff is felt.

22. The catheter of claim 19 wherein the tubes are of different diameters.

23. The catheter of claim 22 wherein only one tube has a lumen large enough to allow drawing blood from the patient.

24. A dual-lumen catheter suitable for surgical implantation in a patient through a subcutaneous tunnel having a point of entry to the skin and a point of entry to the vessel, comprising:
(a) two plastic tubes attached side-by-side to form a figure-8, dual-lumen body, wherein at least one tube has a lumen large enough to allow drawing blood from the patient;
(b) a plastic fill-in portion having segments bonded to the body on opposite sides of the figure-8 to provide a substantially convex, smoothly curving outer locus and bridging the junction of said two tubes, being sufficiently long that the fill-in portion extends between the point of entry to the skin and the point of entry to the vessel, upon implantation, so that the fill-in portion reduces blood leakage at the point of entry to the vessel when the vessel is secured with a ligature and reduces passage of bacteria along the body at the point of entry to the skin, and having a smoothed surface to substantially eliminate tissue growth into the matrix of the fill-in portion; and (c) a cuff positioned on the fill-in portion between the point of entry to the skin and the point of entry to the vessel, to promote tissue in-growth upon implantation, which will fix the catheter within the patient after implantation and which will reduce the passage of bacteria along the intermediate section.

25. The catheter of claim 19 or claim 24 wherein, upon implantation, the portion of the catheter within the vessel is substantially entirely the figure-8, dual-lumen body and wherein, as a consequence, the fill-in portion at the point of entry to the vein ends substantially at the inside of the vessel.

26. The catheter of claim 24 wherein the cuff is positioned substantially midway between the point of entry to the skin and the point of entry to the vessel upon implantation.

27. The catheter of claim 24 wherein the tubes are of different diameters.

28. The catheter of claim 1, claim 14, claim 19, or claim 24, further comprising:
(a) a splitter to detach the tubes near one end of the body and to eliminate further detachment; and
(b) a connector for each detached tube to allow connection of each tube to a fluid reservoir.

29. A dual-lumen catheter suitable for surgical implantation in a patient through a subcutaneous tunnel having a point of entry to the skin and a point of entry to the desired vessel, comprising:
(a) two tubes attached side-by-side to form a figure-8, dual-lumen body;
(b) a first fill-in portion on the body, having a substantially convex, smoothly curving outer locus and bridging the junction of said two tubes, positionable at the point of entry to the skin to reduce the passage of bacteria along the body; and
(c) a second fill-in portion on the body, having a substantially convex, smoothly curving outer locus and bridging the junction of said two tubes, positionable at the point of entry to the vessel to reduce blood leakage when the vessel is secured with a ligature.

30. The catheter of claim 29 wherein the first and second fill-in portions are connected with an intermediate fill-in portion so that the catheter appears to have only one fill-in portion which is sufficiently long to allow contact of the fill-in portion at both the point of entry to the skin and the point of entry to the vessel.

31. The catheter of claim 29 or claim 30 wherein:
(a) the tubes are plastic;
(b) at least one tube has a lumen large enough to allow drawing blood from the patient;
(c) the fill-in portions are plastic;
(d) each fill-in portion is bonded to the body in segments attached to opposite sides of the figure-8; and
(e) each fill-in portion has a smoothed surface to substantially eliminate tissue growth into the matrix of the fill-in portion.

32. A method of surgically implanting a figure-8, dual-lumen catheter, comprising the steps of:
(a) creating a subcutaneous tunnel between a point of entry to the skin and a point of entry to a vessel;
(b) inserting a figure-8, dual-lumen catheter through the tunnel into the vessel;
(c) reducing fluid leakage from the vessel by contacting the vessel with a fill-in portion on the catheter, having a substantially convex, smoothly curving outer locus and bridging the junction of the two tubes that form the figure-8, dual-lumen catheter; and
(d) reducing passage of bacteria into the tunnel by contacting the skin with a fill-in portion on the catheter, having a substantially convex, smoothly curving outer locus and bridging the junction of the two tubes that form the figure-8, dual-lumen catheter.

33. The method of claim 32 wherein the step of reducing fluid leakage further includes the substep of securing the vessel about the catheter with ligature.

34. The method of claim 33, further comprising the step of positioning a cuff on the catheter between the point of entry to the skin and the point of entry to the vessel.

35. The method of claim 34 wherein the step of positioning the cuff places the cuff substantially midway between the point of entry to the skin and the point of entry to the vessel.

36. The method of claim 33 wherein the vessel is selected from the group consisting of the right external jugular, the left external jugular, the right cephalic, the left cephalic, or the femoral veins.

37. The method of claim 33 wherein the vessel is the right external jugular vein.

38. The method of claim 33 wherein the tunnel is between about 4 and 6 inches (about 10-15 cm) long.

39. The method of claim 33, further comprising the step of extending the catheter into the vessel until the tip of the catheter reaches the right atrium.

40. The method of claim 33, further comprising the step of trimming the tip of the catheter before inserting the catheter into the tunnel to bias the dual lumen so that one tube is between about 1 to 10 cm shorter than the other tube.

* * * * *